United States Patent [19]

Simpson

[11] Patent Number: 4,616,648

[45] Date of Patent: Oct. 14, 1986

[54] DEVICE FACILITATING THE EXCHANGE OF DILATATION CATHETERS DURING AN ANGIOPLASTY PROCEDURE

[75] Inventor: John B. Simpson, Woodside, Calif.

[73] Assignee: Devices for Vascular Intervention, Palo Alto, Calif.

[21] Appl. No.: 689,656

[22] Filed: Jan. 8, 1985

[51] Int. Cl.⁴ ............................................. A61B 17/00
[52] U.S. Cl. .............................. 128/303 R; 128/344; 128/348.1; 604/95; 604/159
[58] Field of Search .................... 128/325, 348.1, 344, 128/303 R, 748; 604/96, 159, 161, 164, 171, 95, 170

[56] References Cited

U.S. PATENT DOCUMENTS 3,774,605 11/1973 Jewett .................................. 604/159
4,401,433 8/1983 Luther ................................. 604/159

*Primary Examiner*—Michael H. Thaler
*Attorney, Agent, or Firm*—Flehr, Hohbach, Test Albritton & Herbert

[57] ABSTRACT

Device facilitating the exchange of dilatation catheters during an angioplasty procedure by the use of an exchange wire in which the exchange wire extends through the dilatation catheter into a predetermined position in a vessel of a patient. The device includes first friction rollers engaging the dilatation catheter for advancing or retracting the dilatation catheter and second friction rollers engaging the exchange wire for advancing or retracting the exchange wire. A rotatable member is provided for causing operation of said first and second friction rollers in substantial synchronism and causing movement of the dilatation catheter in one direction and the movement of the exchange wire in an opposite direction so that the distal extremity of the exchange wire remains in a predetermined position in the vessel of the patient during the time that a dilatation catheter is being inserted or being removed from the vessel of the patient.

12 Claims, 8 Drawing Figures

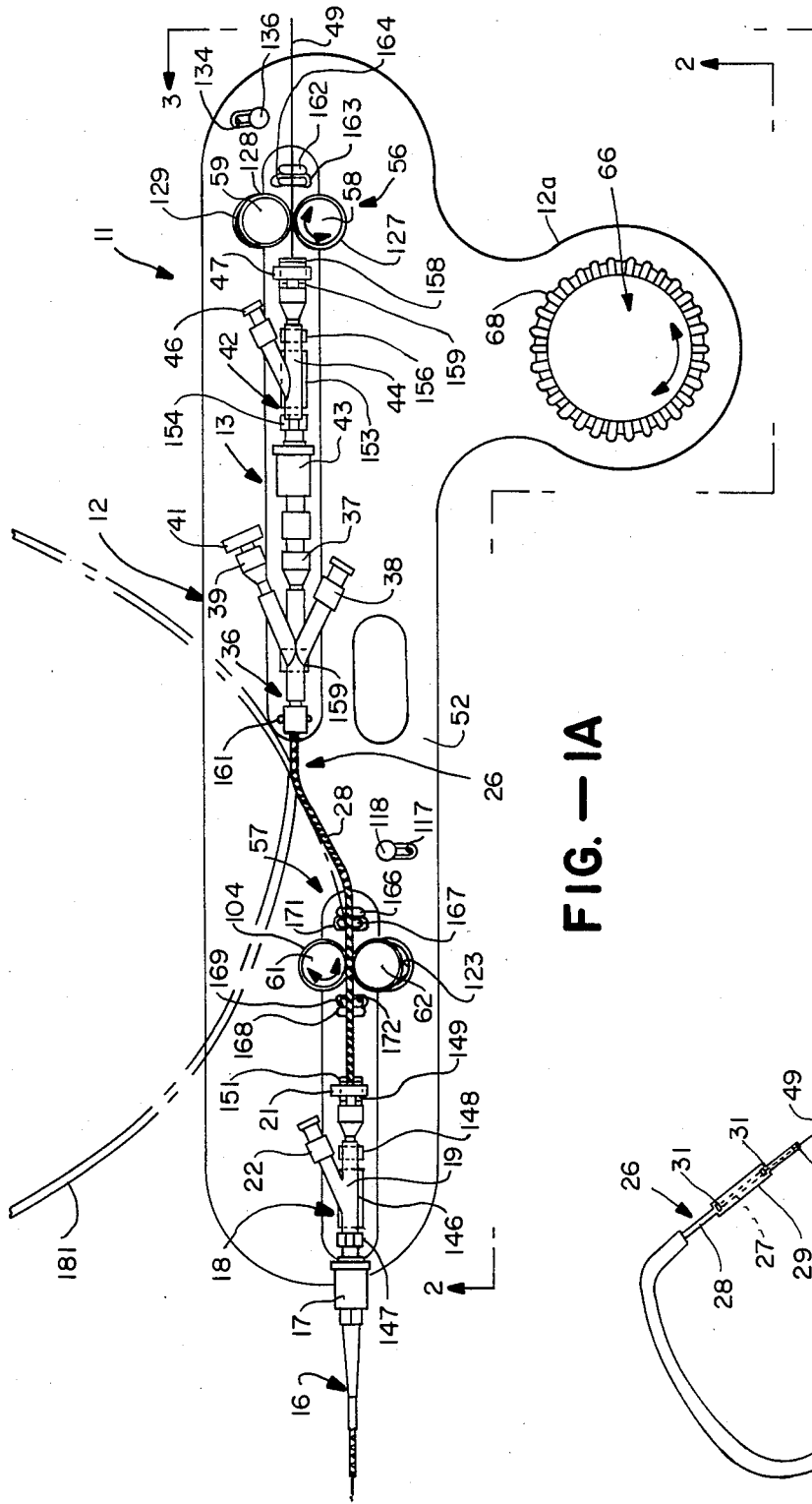
FIG.—1A
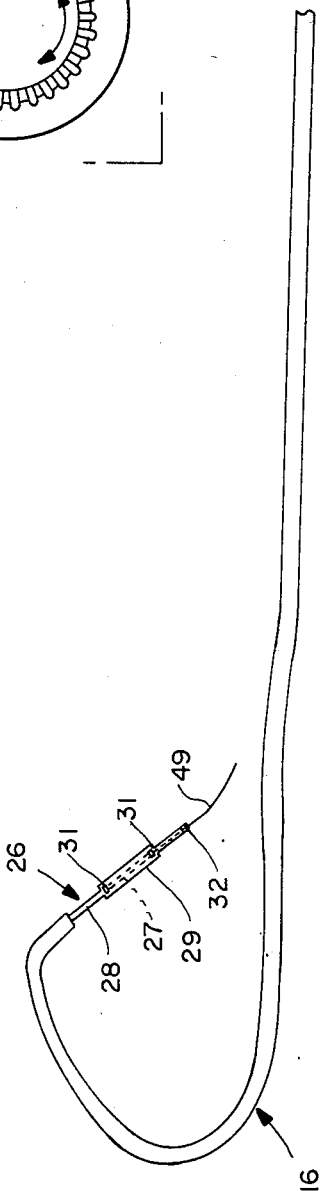
FIG.—1B

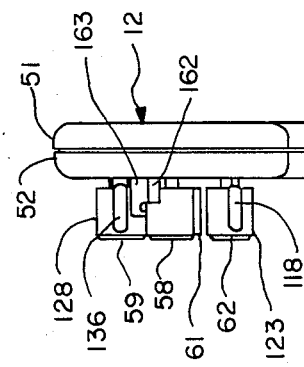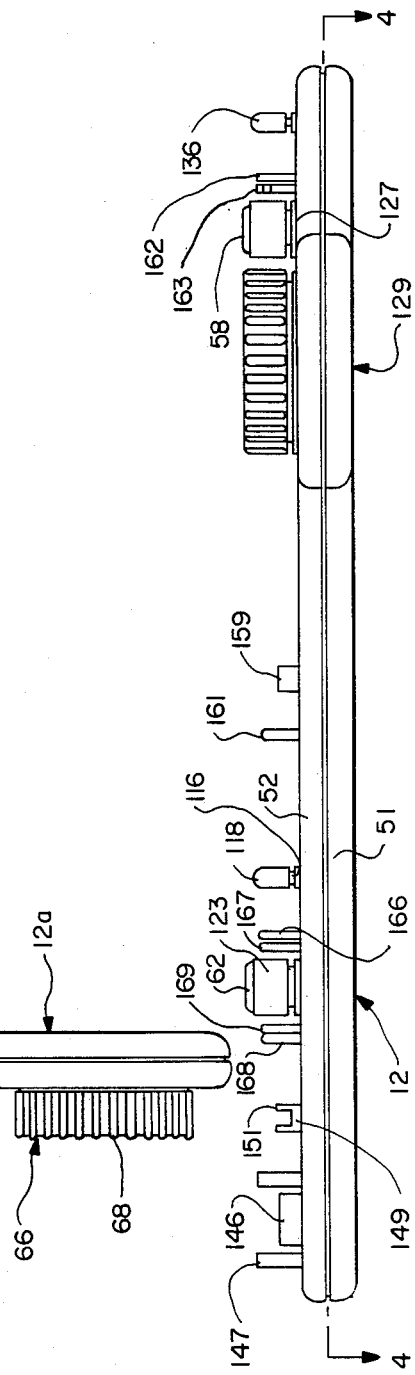

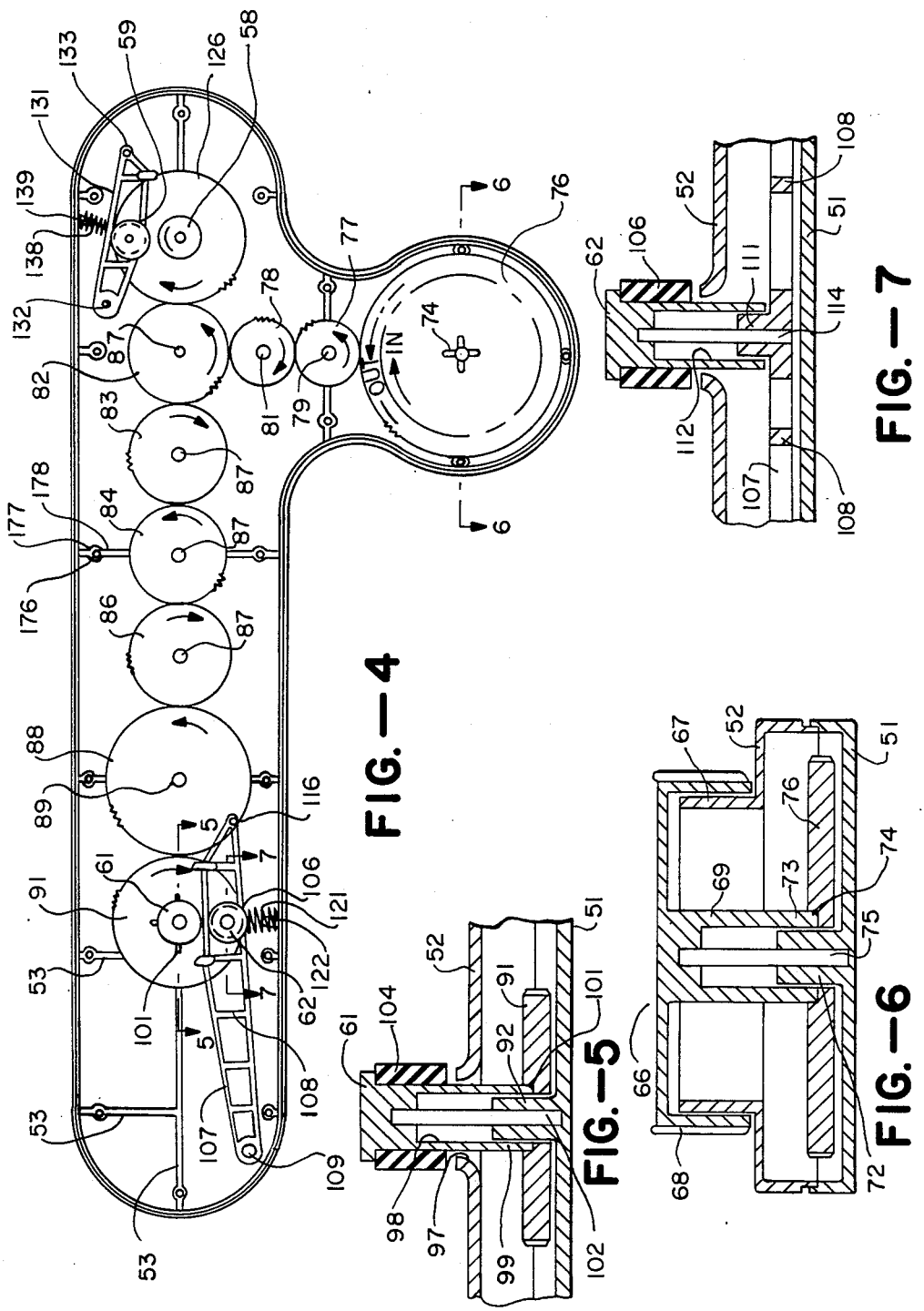

DEVICE FACILITATING THE EXCHANGE OF DILATATION CATHETERS DURING AN ANGIOPLASTY PROCEDURE

This invention relates to a device facilitating the exchange of dilatation catheters during angioplasty procedure by the use of an exchange wire which is adapted to extend through the dilatation catheters.

In the past, there has been an exchange wire utilized in connection with angioplasty procedures in which one dilatation catheter could be substituted for another. In this porcedure, it is important that when the dilatation catheter is being removed that the distal extremity of the exchange guide wire not be disturbed. in other words, its precise position in the blood vessel should be retained. The procedure which has been utilized in the past generally requires two operators (usually both doctors) to achieve the removal of a dilatation catheter over the exchange wire and for the insertion of another dilatation catheter over the exchange wire. In addition to requiring two operators, it has been necessary to more or less continuously view the exchange procedure under x-rays to ascertain that the exchange guide wire position in the blood vessel is not being disturbed. In order to overcome these manpower problems and the excessive use of x-rays, it is desirable to provide a device which can accomplish this procedure and at the same time, accomplish the same with greater precision without the use of x-rays.

In general, it is an object of the present invention to provide a device for facilitating the exchange of dilatation catheters during an angioplasty procedure which may be operated by a single individual.

Another object of the invention is to provide a device of the above character in which the exchange can be accomplished with great precision.

Another object of the invention is to provide a device of the above character in which the exchange can be accomplished without the use of x-rays for viewing the exchange procedure.

Another object of the invention is to provide a device of the above character which can be readily manufactured.

Another object of the invention is to provide a device of the above character which is intended for a single use and is disposed of after use.

Additional objects and features of the invention will appear from the following description in which the preferred embodiment is set forth in conjunction with the accompanying drawings.

FIG. 1A is a top plan view of a device for facilitating the exchange of dilatation catheters and in addition shows a portion of the angioplasty assembly utilized mounted on the device.

FIG. 1B is an enlarged portion of a distal extremity of the angioplasty assembly shown in FIG. 1A.

FIG. 2 is a side elevational view looking along the line 2—2 of FIG. 1A showing the device of FIG. 1A with the angioplasty assembly removed.

FIG. 3 is an end elevational view looking along the line 3—3 of the device shown in FIG. 1A with the angioplasty assembly removed.

FIG. 4 is a cross sectional view taken along the line 4—4 of FIG. 2.

FIG. 5 is a cross sectional view taken along the line 5—5 of FIG. 4.

FIG. 6 is a cross sectional view taken along the line 6—6 of FIG. 4.

FIG. 7 is a cross sectional view taken along the line 7—7 of FIG. 4.

In general, the device for facilitating the exchange of dilatation catheters during an angioplasty procedure is accomplished by the use of an exchange wire in which the exchange wire extends through the dilatation catheter and has its distal extremity positioned in a vessel. First means is provided for frictionally engaging the dilatation catheter for advancing or retracting the dilatation catheter. Second means is provided for frictionally engaging the exchange wire for advancing or retracting the exchange wire. Means is provided for causing operation of the first and second means in substantial synchronism whereby when the dilatation catheter is moved in one direction the exchange wire is moved in an opposite direction so that a dilatation catheter can be removed from a vessel while retaining the distal extremity of the exchange wire in a predetermined position and for introducing another dilatation catheter over the exchange wire while retaining the exchange wire in a predetermined position.

More particularly, the device 11 for facilitating the exchange of dilatation catheter during an angioplasty procedure is shown in FIGS. 1-4. It consists of a housing 12 which carries an angioplasty assembly 13 with which the device is to be used as hereinafter described. The angioplasty assembly 13 is of a conventional type such as that supplied by Advanced Cardiovascular Systems, Inc. of Mountain View, Calif. and consists of a guiding catheter 16. The guiding catheter 16 includes a hemostatic rotater 17, and a distal side arm adapter 18. The side arm adapter 18 includes a main arm 19 on which is mounted a rotatable knob 21 and a side arm 22. The angioplasty assembly 13 also includes a dilatation catheter 26. The dilatation catheter is provided with first and second lumens (not shown) which are formed by tubular members 27 and 28 with the tubular member 27 extending through the tubular member 28. The tubular member 28 is provided with an integrally formed balloon 29. A pair of radiopaque markers 31 are carried by the inner tubular member 27 and are positioned to generally define the outer extremities of the balloon 29. An additional radiopaque marker 32 is provided on the distal extremity of the tubular member 28 for identifying the distal extremity of the dilatation catheter 26. The proximal extremity of the dilatation catheter 26 carries an intermediate side arm adapter 36.

The side arm adapter 36 includes a main arm 37 and side arms 38 and 39. The side arm 39 carries a rotatable knob 41.

The angioplasty assembly 13 also consists of a proximal side arm adapter 42 mounted upon a hemostatic rotater 43. The hemostatic rotater 43 is mounted on the main arm 37 of the intermediate side arm adapter 36. The side arm adapter 42 includes a main arm 44 and a side arm 46. The main arm 44 is provided with a rotatable knob 47. An exchange wire 49 extends through the main arm 42 of the proximal side arm adapter 42 through the side arm adapter 36 of the dilatation catheter 26 and through the end of the dilatation catheter 26 as shown in FIG. 1B.

The housing 12 of the device 11 is elongate as is shown and is provided with a large rounded protrusion 12a adjacent at one end of the same. The housing 12 consists of two parts or half shells 51 and 52 formed of a suitable material such as plastic. The half shells 51 and 52 are provided with a plurality of reinforcing ribs 53. Means is provided on the housing 12 for frictional engaging the exchange wire 49 of the angioplasty assembly 13 and for engaging the dilatation catheter 26 of the angioplasty assembly. The frictionally engaging means consists of a first means 56 and a second means 57. The first means 56 consists of a drive roller 58 and a idler roller 59 whereas the second means consists of a drive roller 61 and an idler roller 62.

Synchronous drive means is provided for causing rotation of the drive rollers 58 and 61 and includes a hand operated knob 66 which is carried by the housing 12. The knob 66 is mounted on the protrusion 12a of the housing 12. The knob 66 is generally cylindrical in form and is rotatably mounted over a cylindrical protrusion 67 formed integral with the top half shell 52. The knob 66 is provided with a plurality of circumferentially spaced vertically extending ribs 68 to facilitate grasping the outer circumference of the knob by the hand of the operator. The knob 66 is provided with a centrally disposed hub 69 which depends downwardly. The hub 69 is provided with a cylindrical recess 71 opening downwardly and loosely fitting over an upwardly extending boss 72 formed integral with the bottom shell 51. The bottom extremity of the hub 69 is provided with downwardly extending keys 73 which are adapted to seat in or mate with recesses 74 provided in a main drive gear 76 which is rotatably mounted upon the upwardly extending boss 72. The knob 66 is retained on the housing by a pin 75 which extends through the boss and extends upwardly into the hub 69.

The main drive gear 76 engages idler gears 77 and 78 rotatably mounted upon upwardly entending bosses 79 and 81 formed integral with the lower top half shell 52. The idler 78 engages and drives a gear 82. The gear 82 drives gear 83, gear 83 drives gear 84 and gear 86 drives gear 88. The gears 82, 83, 84 and 86 are all of the same size and are rotatably mounted on upstanding bosses 87 provided in the top or upper half shell 52. The gear 86 drives a gear 88 which is mounted on a boss 89. The gear 88 drives a gear 91. The gear 91 is mounted on a boss 92 also formed integral with the bottom or lower half shell 51.

The gear 91 drives the roller 61 which extends upwardly through an opening 97 provided in the top or upper shell 52. The roller 61 is generally cylindrical as shown and is provided with a cylindrically downwardly opening recess 98 so that the roller fits over the boss 92. The roller 61 is provided with downwardly extending keys 99 which fit into or mate with recesses 101 provided in the gear 91. The roller 61 is retained on the housing 12 by a pin 102 which extends through the boss 92 and extends upwardly into the roller 61.

A sleeve 104 is provided on a roller 61 and is formed of a suitable elastomeric material such as Neoprene. It is desirable that the sleeve be formed of a material which will not readily oxidize. The material should be characterized in having high friction at the surface while still being compliant so as not to damage the dilatation catheters which are engaged thereby. It should have a hardness ranging from 20 to 60 Shore A durometer.

The idler roller 62 cooperating with the roller 61 is provided with a similar sleeve 106. The idler roller 62 is carried by a release lever 107 which is provided with reinforcing ribs 108. The lever is pivotally mounted in the housing 12 upon a pin 109. The lever 107 is provided with an upwardly extending cylindrical boss 111 which extends into a cylindrical recess 112 provided in the roller 62 (see FIG. 7). A pin 114 extends upwardly through the release lever 107 and into the roller 62 and secures the idler roller 62 to the release lever 107.

Means is provided for operating the release lever 107 and consists of a pin 116 which is mounted on the outer extremity of the release lever 107 and extends upwardly through an arcuate slot 117 provided in the upper shell 52. A knob 118 is mounted on the pin 116 and is adapted to be engaged by the hand. Means is provided for yieldably urging the idler roller 62 into frictional engagement with the drive roller 61 and consists of a coil spring 121 which has one end seated within a well provided in the release lever 107 and having the other hand seated on a protrusion 122 carried by the lower shell 51. When the knob is engaged by a hand, the release lever can be operated to move the idler roller 62 out of frictional engagement with the idler roller 61 against the force of the spring 121.

To accommodate this movement of the idler roller 62, an elongate slot 123 is provided in the upper shell 52.

The gear 82 in addition to driving the gears hereinbefore described to drive the drive roller 61 also causes rotation of a gear 126 which is hereinafter described causes rotation of the driver roller 58. The gear 126 is connected to the drive roller 58 in the same manner that the gear 91 is connected to the roller 61 and therefore this connection will not be described in detail. The roller 58 is provided with a sleeve 127 and similarly, the idler roller 59 is provided with a sleeve 128. Sleeves 127 and 128 can have the same characteristics as the sleeves 104 and 106. The idler roller 59 extends through an arcuate slot 129 provided in the upper shell 52 and is mounted upon a release lever 131 in a manner similar to that to which the idler roller 62 is mounted upon the release lever 107. The release lever 131 has one end pivotally mounted in the housing 12 by a pin 132. The roller 59 is mounted intermediate of the ends of the release lever 131. The other end of the release lever 131 is provided with a pin 133 which extends upwardly through an arcuate slot 134 provided in the upper shell 52. A knob 136 is mounted on the pin 133 and is provided to permit a finger of the hand to move the release lever so as to move the idler roller 59 out of engagement with the drive roller 58 against the yieldable force of a spring 138 which has one end mounted in a well provided in the release lever 131 and having the other end seated on a protrusion 139 carried by the lower shell 51. The springs 121 and 139 are sized so as to provide sufficient frictional engagement between the rollers but insufficient to crush the dilatation catheter 26. It has been found that a force much in excess of two pounds tends to crush the dilatation catheter 26 and that a force of approximately one and one-half pounds is adequate.

It will be noted that the dilatation catheter 28 which is engaged by the roller 61 and 62 has a diameter which is greater than the diameter of the exchange wire 49 which is engaged by the rollers 58 and 59. Since it is an important feature of this invention that the dilatation catheter 28 and the exchange wire 49 be moved equal distances, there is a need to compensate for this difference in diameters. As can be appreciated, this difference in diameters can be compensated for in either of two ways, either by rotating the two sets of rollers at different speeds to compensate for the difference in diameters or to change the diameters of the two sets of rollers. In the present embodiment, the two sets of rollers are driven at the same speed and the diameters of the two sets of rollers are different. The diameters of the drive roller 58 and the idler roller 59 engaging the exchange wire 49 are made slightly smaller than the diameters of the rollers 61 and 62 engaging the dilatation catheter 26. By way of example, it has been found that when the diameters of the rollers 58 and 59 are decreased by approximately 0.030ths of an inch with respect to the diameters of the rollers 61 and 62 that this difference in diameters will compensate for the differences in the diameters of the dilatation catheter 26 and the exchange wire 49. This change in thickness can be readily accommodated by providing elastomeric sleeves of the desired diameters on the rollers.

The gearing which is hereinbefore described which interconnects the knob 66 with the drive gears 91 and 126 for the drive rollers 61 and 58 respectively is such that the gears 91 and 126 will be driven at the same speed. The gearing has also been selected that with approximately ten full revolutions of the knob 66 a complete dilatation catheter exchange can be accomplished as hereinafter described. Thus the diameter of the gears 76 can be two inches with the gears 77 and 78 having a diameter of $\frac{3}{4}$ of an inch and the gears 82, 83, 84 and 86 having a diameter of one inch, the gear 88 a diameter of $2\frac{1}{4}$ inches and the gears 91 and 126 having a diameter of two inches. The teeth on the gears can have any suitable pitch 12, for example, 32 pitch. They also can have any desired number of teeth as, for example, the main drive gear 76 can have 96 teeth with the other gears having proportional numbers of teeth.

The gears can be formed of any suitable material such as plastic. It is desirable that they be formed of a self lubricating material such as Nylon. In addition to the gears, the rollers 58, 59, 61 and 62, as well as the drive knob 76 should be formed of a similar self lubricating material.

Retaining means is provided on the housing 12 for supporting the angioplasty assembly 13 and for securing it thereto. As shown particularly in FIG. 1A, this means consists of means for carrying the distal side arm adapter, the intermediate side arm adapter 36 and the proximal side arm adapter 42. Means for securing the distal side arm adapter 18 to the housing 12 consists of a rectangular block 146 formed intergal with the top shell 52 upon which the side arm adapter 18 rests and two pairs of spaced apart upstanding clip members 147 and 148 disposed adjacent opposite ends of the block 146 and adapted to frictionally engage cylindrical portions of the side arm adapter 18. The clips 147 and 148 are formed integral with the top shell 52. The clips 147 and 148 serve to prevent lateral movement of the distal side arm adapter 18. The retaining means for the side arm adapter 18 also includes means for inhibiting movement longitudinally of the block 146 and consists of another small block 149 which is provided with a pair of upstanding spaced apart ears 151. The spaced apart ears 151 are spaced apart a sufficient distance so as to receive the rotatable knob 21 and to permit rotation of it while the distal side arm adapter 18 is retained within the clips 147 and 148. By positioning the rotatable knob 21 between the spaced apart members 151, the distal side arm adapter 18 is restricted from substantial movement longitudinally of the block 146.

Similar retaining means is provided for retaining the proximal side arm adapter 42 on the housing 12 and consists of a block 153 with two pairs of spaced apart clips 154 and 156 mounted adjacent opposite ends of the block 153. It also includes a block 157 which is provided with spaced apart upstanding ears 158 which are adapted to receive the rotatable knob 47 of the proximal side arm adapter 52.

The retaining means for retaining intermediate side arm adapter 36 on the housing 12 consists of a smaller block 159 and a pair of upstanding pins 161 disposed on the distal side of the block 159. The intermediate side arm adapter 36 is adapted to rest upon the block 156 and the distal extremity of the side arm adapter 36 is adapted to rest between the pins 161. The blocks and the clips as well as the members hereinbefore described all are formed integral with the top shell 52 and are formed of the same material as the top shell 52.

Means is provided for guiding the exchange wire 49 in through and between the rollers 58 and 59 and consists of a pair of upstanding hook members 162 and 163 with one hook member 162 being formed integral with the top shell 52 and with the other hook member 163 extending through a slot 164 provided in the top shell 52 and being secured to the release lever 131. It can be seen from FIG. 1A, that the hook members 162 and 163 are offset with respect to each other so that the hook member 163 can overlap the hook member 162. To insert the exchange wire 49 between the hook members 162 and 163, the hook member 163 is moved away from the hook member 162 for use of the knob 136 to shift the position of the release lever to move the hook member 163 as well as the idler roller 59 into position so that the exchange wire can be positioned between the hook members 162 and 163 and between the rollers 58 and 59. As soon as the knob 136 is released, the spring 138 will urge the release lever 131 into a direction so that the idler roller 59 engages the exchange wire 49 and so that the hook member 163 moves into cooperating engagement with the hook member 162 to retain the exchange wire therein so it cannot be moved in a vertical or lateral direction with respect to the housing 12.

Similar means is provided for guiding the tubular member 28 of the dilatation catheter 26 between the rollers 61 and 62 and consists of a pair of hook members 166 and 167 and a second pair of hook members 168 and 169. The hook members 166 and 168 are formed integral with the top shell 52 and are upstanding therefrom. The hook members 167 and 169 extend through slots 171 and 172 formed in a top shell 52 and are mounted upon the release lever 107. The hook members 168 and 169 are offset with respect to each other in the same manner as the hook members 162 and 163. Upon operation of the knob 118 to move the idler roller 62 away from the drive roller 61, the hook members 167 and 169 will be moved with the idler roller so as to permit the tubular member 28 to be inserted between the rollers 61 and 62 and to be seated between the pairs of hook members 166, 167, 168 and 169 disposed on opposite sides of the rollers 61 and 62. When the knob 118 is released, the rollers 61 and 62 will frictionally engage the tubular member 28 and the hook members will retain the tubular member 28 within the hook members to prevent lateral and vertical movement of the tubular member 28.

In assemblying the device 11, the gears and release levers can be mounted in the top shell 52. After this has been accomplished, the bottom shell 51 is secured to the top shell 52 in a suitable manner. For example, male pins 176 can be provided on the bottom shell 51 and female bosses 177 can be provided on the top shell. The bosses 177 can be provided with holes 178 which are adapted to receive the pins 176 and to provide an interference fit so that when the two halves are pressed together, they cannot hereafter be separated. This type of construction is utilized because the entire device is a throwaway device after use.

Operation and use of the device in connection with an angioplasty procedure may now be briefly described as follows. Let it be assumed that an angioplasty procedure is underway and that a guiding catheter 16 has been inserted into the patient and that it is disposed in a heart vessel. Also let it be assumed that a dilatation catheter 26 has been inserted into the guiding catheter with the use of a conventional guide wire and that it has been positioned in the desired location to perform a balloon dilatation at the stenosis in the heart vessel. Let it be assumed that a first balloon dilatation has been accomplished but that the attending physician desires to utilize a dilatation catheter having a larger balloon to create the larger opening in the stenosis. To accomplish this, the guide wire is removed leaving the dilatation catheter 26 in place and an exchange wire 49 is inserted through the dilatation catheter 26 until its distal extremity is in the same position as the guide wire previously used for the dilatation catheter. As soon as this has been accomplished, the device 11 of the present invention can be utilized by positioning the housing 12 along the side of the leg of the patient in such a manner that the portion 12a of the housing extends upwardly from the leg of the patient so that the knob 66 can be grasped by the attending physician. The physician then inserts the angioplasty assembly 13 into the device by first operating the knob 136 to move the idler roller 59 and the hook 163 to out-of-way or out-of-engagement positions. The exchange wire 49 is then inserted between the hook members 162 and 163 and between idler roller 59 and the drive roller 58. Thereafter, the knob 136 can be released so that the exchange wire 49 is frictionally engaged by the rollers 58 and 59. Thereafter, the proximal side arm adapter 42 is slipped between the clips 154 and 156 so that it is seated upon the block 153 with the knob 47 disposed between the members 158.

The intermediate side arm adapter 36 is also positioned on the block 159 with its distal extremity between the upstanding pins 161. The knob 118 is then engaged to move the idler roller 62 into an out-of-the-way or disengaging position and the tubular member 28 of the dilatation catheter 26 is positioned between hook members 168 and 169 and hook members 166 and 167 and between the rollers 61 and 62. Thereafter, the knob 118 is released to permit the hook members to engage the dilatation catheter 26 and to permit the idler roller 62 to move the tubular member 28 of the dilatation catheter 26 into frictional engagement with the drive roller 61. Thereafter, the distal side arm adapter 18 is positioned over the block 146 and slipped into the clips 147 and 148 with the knob 21 between disposed between the members 151 on the block 149.

As soon as the angioplasty assembly 13 has been mounted on the housing 12, the physician is ready to undertake the exchange procedure. This is accomplished by rotating the knob 66 in a counterclockwise direction which causes the drive rollers 58 and 61 to be rotated in counterclockwise directions. It should be noted that although rollers 58 and 61 are being rotated in the same direction as the knob 66, they are located on opposite sides of the respective elements they engage, that is, the drive roller 58 is in engagement with the exchange wire 49 on the side facing the knob 66 whereas the drive roller 61 engages the tubular member 28 on the side opposite the side facing the knob 66 and therefore exert frictional forces upon the respective members in directions which are opposite to each other. Thus upon counterclockwise rotation of the knob 66, the exchange wire 49 is moved to the left as viewed in FIG. 1A, and the tubular member 28 is moved to the right as viewed in FIG. 1A. As explained previously, the diameter of the rollers 58 and 59 and rollers 61 and 62 are such so that for every increment that the tubular dilatation catheter is advanced, the exchange wire 49 is advanced by a similar increment. This means that as the dilatation catheter 26 is withdrawn from the blood vessel through the guiding catheter 16, the exchange wire 49 is inserted with respect to the tubular member so that the distal extremity of the exchange wire 49 remains in the exact same position within the blood vessel in the body. As the dilatation catheter 26 is withdrawn, a loop 181 is formed in the dilatation catheter as shown in broken lines in FIG. 1A. As the dilatation catheter 26 is being removed, a larger and larger loop 181 is formed. This withdrawal procedure is continued until the distal extremity of the dilatation catheter 26 is clear of the rollers 61 and 62 and the rollers 61 and 62 engage the exchange wire 49. When the distal extremity of the dilatation catheter clears the knob 21, there may be a tendency for blood to flow from the guiding catheter 16 and the knob 21 is tightened down so as to inhibit this flow of blood.

As soon as the distal extremity of the dilatation catheter 26 has cleared the rollers 61 and 62, the proximal portion of the angioplasty assembly 13 is lifted out of the means provided for securing the intermediate side arm adapter 36 and the proximal side arm adapter 42 to the housing 12. As the assembly 13 is removed from the clips on the housing 12, one hand is utilized for operating the knob 136 so that the exchange wire 49 is released from between the rollers 58 and 59 and from between the hook members 162 and 163. The dilatation catheter 26 then can be slipped off of the exchange wire. As soon as this has been accomplished, another dilatation catheter having a baloon of the desired size can then be slipped on to the exchange wire 49. In slipping the new dilatation catheter over the exchange wire 49, a loop similar to loop 181 can be formed. The intermediate and proximal side arm adapters 36 and 42 can then be snapped into place onto the housing 12 in a manner hereinbefore described. As soon as this has been accomplished, the knob 66 can be rotated in a clockwise direction to cause the dilatation catheter to be introduced into the guiding catheter 16 and at the same time causing the exchange wire 49 to be retracted by a corresponding amount so that the distal extremity of the exchange wire 49 remains in the same precise position during the time that the new dilatation catheter is being advanced until the balloon of the dilatation catheter reaches the desired position. With the devce of the present invention there is a one-to-one correspondence between retraction and insertion so that the distal extremity of the exchange wire remains in the same position throughout the procedure.

If the physician desires to utilize a different dilatation catheter, the same procedure can be readily accomplished within a relatively short period of time so that a plurality of dilatation catheters can be utilized in connection with forming an opening in a single stenosis if desired.

After the angioplasty procedure has been accomplished, the entire angioplsty assembly 13 can be removed from the patient. The angioplasty assembly 13 and the device 11 can then be disposed of. The device 11 is to be a throw-away device to be utilized with only a single angioplasty procedure to avoid any possible contamination. It should be appreciated, however, that if desired the device 11 can be constructed of materials which would make it possible to sterilize the same so it can be utilized for successive angioplasty procedures if that is desirable. To make this possible, it is merely necessary to construct a device of materials which would facilitate sterilization.

In conjunction with the foregoing, it should be noted thr four rollers have been utilized for the insertion and extraction procedures hereinbefore described. It should be appreciated that as few as three rollers could be utilized for this procedure by utilizing a single drive roller and having idler rollers engaging opposite sides of the drive roller with the dilatation catheter being disposed between one idler roller and the drive roller on one side and the exchange wire being disposed between the other idler roller and the drive roller. This procedure, however, would make it more difficult to compensate for the difference in diameters between the exchange wire and the dilatation catheter.

The use of the device of the present invention is particularly advantageous in that it makes it possible for a single physician to accomplish the exchange procedure with great precision and without the necessity of continuously observing the exchange procedure under x-rays. Therefore this greatly reduces the amount of exposure that the patient receives from x-rays during an angioplasty procedure.

What is claimed is:

1. In a device facilitating the exchange of dilatation catheters during an angioplasty procedure by the use of an exchange wire in which the exchange wire extends through the dilatation catheter into a predetermined position in a vessel of a patient, first means frictionally engaging the dilatation catheter for advancing or retracting the dilatation catheter, second means frictionally engaging the exchange wire for advancing or retracting the exchange wire, means for causing operation of said first and second friction means in substantial synchronism and causing movement of the dilatation catheter in one direction and the movement of the exchange wire in an opposite direction to form a loop of changing size of the catheter with the exchange wire therein while retaining the distal extremity of the exchange wire and the proximal extremity of the dilatation catheter in predetermined positions during the time that a dilatation catheter is being inserted or being removed from the vessel of the patient.

2. A device as in claim 1 in which the angioplasty assembly includes side adapters, together with a housing for mounting said first and second means, said means for causing operation of said first and second means and means for releasably securing the side arm adapters to the housing.

3. A device as in claim 2 wherein said first and second means includes first and second drive rollers and first and second idler rollers and means yieldably urging the idler rollers into engagement with the drive rollers wherein said means for causing operation of said first and second means includes a rotatable member and means interconnecting said rotatable member with said first and second drive rollers for causing rotation of said first and second drive rollers.

4. A device as in claim 3 wherein said first and second drive rollers are positioned so that they cause movement of a dilatation catheter and the exchange wire in opposite directions upon rotation of the rotatable member.

5. A device as in claim 4 wherein said means for causing rotation of said first and second drive rollers includes synchronous drive means.

6. A device as in claim 5 together with a housing formed in two parts and wherein said synchronous drive means is disposed between the parts of the housing.

7. A device as in claim 6 wherein the synchronous drive means is a gear train.

8. A device as in claim 3 together with means carried by the housing for yieldably urging the idler rollers into frictional engagement with the drive rollers.

9. A device as in claim 8 together with hand operated means carried by the housing for moving the idler rollers out of engagement with the drive rollers against the force of the yieldable means.

10. A device as in claim 3 together with means for guiding the dilatation catheter and the exchange wire into the drive roller and associated idler roller.

11. A device as in claim 3 wherein the housing is elongate with a protrusion formed thereon and wherein the rotatable member is carried by the protrusion.

12. A device as in claim 2 wherein said means for retaining said side arm adapter on the housing includes means for limiting lateral movement of the side arm adapter on the housing and wherein the side arm includes a knob and means for engaging the knob for limiting movement of the side arm adapter longitudinally for the housing.

* * * * *